United States Patent [19]

Flemming et al.

[11] Patent Number: 5,191,065
[45] Date of Patent: Mar. 2, 1993

[54] PROCESS FOR THE PREPARATION OF TRIPEPTIDES

[75] Inventors: Hans-Wolfram Flemming, Usingen; Manfred Rukwied, Kelkheim; Manfred Schmidt, Weilmünster, all of Fed. Rep. of Germany

[73] Assignee: Hoechst Aktiengesellschaft, Frankfurt am Main, Fed. Rep. of Germany

[21] Appl. No.: 728,028

[22] Filed: Jul. 8, 1991

Related U.S. Application Data

[63] Continuation of Ser. No. 7,438,073, Nov. 20, 1989, abandoned.

[30] Foreign Application Priority Data

Nov. 22, 1988 [DE] Fed. Rep. of Germany ....... 3839379

[51] Int. Cl.$^5$ .................... A61K 37/02; C07K 5/00
[52] U.S. Cl. .................................. 530/331; 530/337; 530/340
[58] Field of Search .................... 530/331, 337, 340

[56] References Cited

U.S. PATENT DOCUMENTS 3,062,804 11/1962 Albertson .......................... 530/337
4,331,592 5/1982 Wissmann et al. ................. 530/340

FOREIGN PATENT DOCUMENTS 0156280 11/1985 European Pat. Off. .
7900602 8/1979 World Int. Prop. O. .

OTHER PUBLICATIONS

Hoppe-Seylers Zeitschrift F. Physiol. Chemie 334, 248 (1964).

*Primary Examiner*—Merrell C. Cashion, Jr.
*Assistant Examiner*—B. Celsa
*Attorney, Agent, or Firm*—Finnegan, Henderson, Farabow, Garrett and Dunner

[57] ABSTRACT

A process for the preparation of tripeptides of the general formula I $$U\text{-}A\text{-}B\text{-}C\text{-}OH \qquad I$$

in which U denotes hydrogen or a urethane protective group and A, B and C denote amino acids, by reaction of a compound of the general formula II $$U'\text{-}B\text{-}OH \qquad II$$

in which U' is a urethane protective group which can be eliminated by hydrogenolysis, with a compound of the general formula III $$H\text{-}C\text{-}OR \qquad III$$

in which R denotes alkyl, by the PPA method, elimination of U', and reacting the resulting compound of the formula IV $$H\text{-}B\text{-}C\text{-}OR \qquad IV$$

with a compound of the formula V $$U\text{-}A\text{-}OH \qquad V$$

in the presence of propylphosphonic anhydride, and finally eliminating R enzymatically.

10 Claims, No Drawings

PROCESS FOR THE PREPARATION OF TRIPEPTIDES

This application is a continuation of application Ser. No. 07/438,073, filed Nov. 20, 1989, now abandoned.

Tripeptides are important intermediates in the synthesis of bioactive peptides such as, for example, the hypothalamus hormone gonadorelin and its analogs. For this purpose the tripeptides must be available in the most straightforward manner possible, on the one hand in good yields and, on the other hand, in high purity. The processes hitherto disclosed for the preparation of tripeptides do not meet these requirements in an optimal manner and are associated with disadvantages, some of which are serious. Thus, for example, even the products prepared by the process described in EP-A 156,280 are contaminated with byproducts which become disadvantageously evident in the subsequent synthetic steps. Thus the object of the present invention is to provide a process for the preparation of tripeptides which does not have the said disadvantages and provides, in a straight-forward manner, products of high purity in good yields.

Accordingly, the invention relates to a process for the preparation of tripeptides of the general formula I

U-A-B-C-OH     I in which
OH denotes a hydroxy substituent
U denotes hydrogen or a urethane protective group
A denotes a natural α-amino acid
B denotes a natural α-amino acid and
C denotes an aromatic α-amino acid,
which comprises reacting a compound of the general formula II

U'-B-OH     II in which U' is a urethane protective group which can be eliminated by hydrogenolysis, and B has the above-mentioned meaning, with a compound of the general formula III

H-C-OR     III in which R represents alkyl having 1 to 4 carbon atoms, H represents a hydrogen and C has the above-mentioned meaning, in the presence of propylphosphonic anhydride, eliminating the protective group U' by hydrogenolysis, reacting the resulting compound of the general formula IV

H-B-C-OR     IV with a compound of the general formula V

U-A-OH     V in the presence of propylphosphonic anhydride, and finally eliminating R enzymatically.

The urethane protective groups representing U are preferably the urethane protective groups customary in peptide chemistry, as are described, for example, in Kontakte Merck 3/79, page 14. The benzyloxycarbonyl and the tert.-butyloxycarbonyl groups are particularly preferred. A urethane protective group U' which can be eliminated by hydrogenolysis is preferably the benzyloxycarbonyl group.

Natural α-amino acids or their derivatives representing A and/or B are preferably Gly, Ala, Ser, Thr, Val, Leu, Ile, Glu, Gln, p-Glu, Tyr, Phe, Trp and His. Ser, Thr, Trp and Phe are particularly preferred.

An aromatic α-amino acid representing C is preferably Tyr or Phe.

R in the general formula IV preferably denotes methyl.

A process in which U and U' denote benzyloxycarbonyl, A denotes Trp, B denotes Ser, C denotes Tyr and R denotes methyl is very particularly preferred.

The formation of a peptide linkage in the presence of propylphosphonic anhydride is known as the PPA method (Angew. Chem. Int. Ed. 19, 133 (1980)). This reaction is preferably carried out in polar solvents such as, for example, dimethylacetamide, dimethylformamide, dimethyl sulfoxide, phosphoric tris(dimethylamide), N-methyl-pyrrolidone or water. However, chloroform, methylene chloride or ethyl acetate are also employed. It is also possible in an advantageous manner to use mixtures of the said solvents with water. An ethyl acetate/water mixture is particularly preferred. The synthesis can be carried out between −10° C. and room temperature. It is preferable to start at about 0° C. and subsequently to raise to room temperature.

The elimination of the U' protective group by hydrogenolysis is advantageously carried out in a known manner with hydrogen on a Pd/C catalyst.

The enzymatic esterolysis in the last reaction step is preferably carried out with trypsin and/or α-chymotrypsin (Hoppe-Seylers Zeitschrift f. physiol. Chemie, 336, 248 (1964)). Trypsin is particularly preferred. Where appropriate, enzymes which are immobilized by known methods on a support are also used, such as described, for example, in EP-A 178,553. In this case, the enzymes are advantageously employed in amounts of 0.01 to 20% by weight relative to the amount of substrate. An amount of 2% by weight of enzyme is particularly preferred.

Examples of solvents which can be employed are water, dimethylformamide, methanol, ethanol, isopropanol, butanol, ethyl acetate, butyl acetate, toluene or methylene chloride. An ethyl acetate/water mixture is preferred. The temperatures are advantageously between 0° and 60° C. A temperature range from 20° to 35° C. is preferred. The pH of the reaction medium is preferably in the range between 4 and 10, particularly preferably between 4 and 8.

The process according to the invention can be carried out in such a way that each intermediate is isolated. However, it is preferably carried out in a one-pot process, that is to say without isolation of the intermediates. The starting compounds of the general formulae II, III and V are known and can be obtained by the customary methods.

The process according to the invention surprisingly provides products of high chemical and optical purity, which can be employed without difficulty in further syntheses. The yields are likewise excellent and are between 40 and 50% based on the amount of the compound of the general formula III employed.

It has to be regarded as particularly surprising that the process according to the invention is distinctly superior, in terms both of purity and of yield, to the process of EP-A 156,280, which has only three stages.

EXAMPLE

Z-Trp-Ser-Tyr-OH a) 350 ml of water are placed in a 2 l stirred apparatus, and 47.8 g (0.200 mol) of Z-Ser-OH, wherein Z represents benzyloxycarbonyl, 46.4 g (0.200 mol) of H-Tyr-OMexHCl, wherein Mex represents OMe-HCl, and 150 g of sodium chloride are introduced. Also added are 700 ml of ethyl acetate and, after everything has dissolved, the pH of the mixture is adjusted to 5.0 by addition of about 25 ml of N-ethylmorpholine. During the addition of about 220 ml (0.42 mol) of PPA solution (w(PPA) in %=50) in about 30 minutes at a maximum of 30° C. (cool somewhat at the end), about 110 ml (0.86 mol) of N-ethylmorpholine are added via a pH-stat pump at pH 5.0. The PPA addition is terminated when a precipitate forms in the reaction mixture. The precipitate is redissolved by subsequent addition of 350 ml of water. The aqueous phase is separated off in a separating funnel and then the ester phase is washed with 700 ml of potassium bisulfate solution (w(KHSO₄) in %=10) and 700 ml of sodium bicarbonate solution (w(NaHCO₃) in %=5). The aqueous phase from the reaction and the wash phases are discarded.

b) About 700 ml of ester phase from the 1st coupling, 200 ml of water and 3.3 g of palladium on carbon w(Pd) in %=2.5 are placed in a 2 l stirred apparatus and a stream of hydrogen is passed in at 25°-30° C. During the reaction the pH is maintained at 4.0 with a pH-stat pump and addition of about 160 ml (0.16 mol) of hydrochloric acid c(HCl)=1 mol/l. After the reaction is complete, when no more hydrochloric acid is consumed, (about 30 minutes) the reaction mixture is filtered through a suction funnel, and the aqueous phase is separated from the ester phase in a separating funnel. The ester phase is discarded.

c) About 430 ml of aqueous phase from the hydrogenolysis and 700 ml of ethyl acetate are placed in a 2 l stirred apparatus and 50.7 g (0.15 mol) of Z-Trp-OH and 125 g of sodium chloride are added. After everything has dissolved, the pH is adjusted to 5.0 with about 19 ml of N-ethylmorpholine. During the addition of about 220 ml (0.42 mol) of PPA solution (w(PPA) in %=50) in about 30 minutes at a maximum of 30° C. (cool somewhat at the end), about 110 ml (0.86 mol) of N-ethylmorpholine are added via a pH-stat pump at pH 5.0. The PPA addition is terminated when a precipitate forms in the reaction mixture. The precipitate is redissolved by subsequent addition of 350 ml of water. The aqueous phase is separated off in a separating funnel, and then the ester phase is washed with 700 ml of potassium bisulfate solution (w(KHSO₄) in %=10) and several times with 700 ml portions of sodium bicarbonate solution (w(NaHCO₃) in %=5) until Z-Trp-OH has been completely removed (according to TLC analysis). The aqueous phase from the reaction and the wash phases are discarded.

d) About 700 ml of ester phase from the 2nd coupling and 700 ml of water are placed in a 2 l stirred apparatus and heated to 35°-40° C., and 1 g of trypsin is initially added. The reaction starts immediately and, during it, the pH is maintained constant at pH 7.0 with about 110 ml (0.11 mol) of sodium hydroxide solution (c(NaOH)=1 mol/l). The reaction lasts about 7 hours and, during this, the rate is increased now and again by further addition of 0.5 g of trypsin. It is complete when trypsin addition now brings about only a slight increase in the rate of absorption of sodium hydroxide solution, or TLC analysis shows hardly any starting material remaining. The reaction solution is clarified through a suction funnel, and the ester phase is separated from the aqueous phase in a separating funnel. The ester phase is discarded.

The aqueous phase is initially extracted by shaking twice at pH 5.8–6.0, by addition and dissolution of 4.0 g of potassium dihydrogen phosphate, with 700 ml of ethyl acetate each time. The ester phases are discarded. The aqueous phase is then extracted by shaking three times at pH 5.0, adjusted by addition of about 5 ml of glacial acetic acid, with 700 ml of ethyl acetate each time. The aqueous phase is discarded. The ester phases contain the tripeptide which, on evaporation to dryness in vacuo, remains in the form of loosely packed crystals. The product is dried in a vacuum oven at 40° C.

Weight: 51.2 g
Yield: 42.0% based on H-Tyr-OMexHCl
Purity: 98.2% (determined with HPLC LiChrosorb Si 60/peptide buffer)

COMPARISON EXAMPLE

Z-Trp-Ser-Tyr-OH was prepared by the process specified in EP-A 156,280.
Yield: 30%
Purity: 78.8% (determined with HPLC LiChrosorb Si 60/peptide buffer)

We claim:

1. A process for the preparation of tripeptides of the general formula I

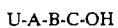
U-A-B-C-OH            I in which
OH denotes a hydroxy substituent,
U denotes hydrogen or a urethane protective group,
A denotes a natural α-amino acid,
B denotes a natural α-amino acid, and
C denotes an aromatic α-amino acid,
comprising the steps of
(1) reacting a compound of the formula II

U'-B-OH            II in which U' is a urethane protective group which can be eliminated by hydrogenolysis, and B and OH have the above-mentioned meanings, with a compound of the formula III

H-C-OR            III in which R represents alkyl having 1 to 4 carbon atoms, H represents a hydrogen, and C has the above-mentioned meaning, in the presence of propylphosphonic anhydride, (2) eliminating the protective group U' by hydrogenolysis, (3) reacting the resulting compound of the formula IV

H-B-C-OR            IV with a compound of the formula V

U-A-OH            V whereby the reaction is carried out in a solvent system consisting essentially of water and one or more compounds selected from the group consisting of chloroform, methylene chloride, butyl acetate, and ethyl acetate, in the presence of propylphosphonic anhydride, and finally (4) eliminating R enzymatically.

2. The process as claimed in claim 1, wherein U denotes benzyloxycarbonyl or tert.-butyloxycarbonyl.

3. The process as claimed in claim 1, wherein A and B independently of each other denote Gly, Ala, Ser, Thr, Val, Leu, Ile, Glu, Gln, p-Glu, Tyr, Phe, Trp or His.

4. The process as claimed in claim 1, wherein A and B independently of each other denote Ser, Thr, Trp or Phe.

5. The process as claimed in claim 1, wherein C denotes Tyr or Phe.

6. The process as claimed in claim 1, wherein U' denotes benzyloxycarbonyl.

7. The process as claimed in claim 1, wherein R denotes methyl.

8. The process as claimed in claim 1, wherein the reactions are carried out in the presence of propylphosphonic anhydride in an ethyl acetate/water mixture.

9. The process as claimed in claim 1, wherein the enzymatic esterolysis is carried out with a compound selected from the group consisting of trypsin, α-chymotrypsin, and a mixture thereof.

10. The process as claimed in claim 1, wherein U and U' denote benzyloxycarbonyl, A denotes Trp, B denotes Ser, C denotes Tyr and R denotes methyl.

* * * * *